United States Patent [19]

Lovrecich et al.

[11] Patent Number: 5,068,111
[45] Date of Patent: Nov. 26, 1991

[54] PHARMACEUTICAL TABLETS AND CAPSULE GRANULATES OF SCLEROGLUCAN AND ACTIVE SUBSTANCE

[75] Inventors: Mara L. Lovrecich, Trieste; Giovanna Riccioni, Rome, both of Italy

[73] Assignee: Vectorpharma International S.p.A., Trieste, Italy

[21] Appl. No.: 324,736

[22] Filed: Mar. 17, 1989

[30] Foreign Application Priority Data

Mar. 17, 1988 [IT] Italy ................................ 19816 A/88

[51] Int. Cl.$^5$ .......................... A61K 9/16; A61K 9/26; A61K 9/52
[52] U.S. Cl. .................................... 424/469; 424/461; 424/465; 424/488; 424/499
[58] Field of Search ............... 424/469, 456, 451, 488, 424/494, 465, 499, 461

[56] References Cited

U.S. PATENT DOCUMENTS

| | | | |
|---|---|---|---|
| 4,178,361 | 12/1979 | Cohen | 424/487 |
| 4,449,983 | 5/1984 | Cortese | 424/473 |
| 4,642,233 | 2/1987 | Urquhart | 424/486 |
| 4,738,850 | 4/1988 | Thakur | 424/470 |

*Primary Examiner*—Thurman K. Page
*Assistant Examiner*—Amy Hulina
*Attorney, Agent, or Firm*—Birch, Stewart, Kolasch & Birch

[57] ABSTRACT

Pharmaceutical tablets and capsule granulates for oral administration, with controlled release of the active substance, comprising scleroglucan and active substance and pharmaceutical acceptable excipients, said tablets being prepared by mechanically mixing said substances in the solid state and directly compressing, and said granulates being prepared by mechanically disgregating said tablets.

2 Claims, No Drawings

PHARMACEUTICAL TABLETS AND CAPSULE GRANULATES OF SCLEROGLUCAN AND ACTIVE SUBSTANCE

FIELD OF THE INVENTION

This invention relates to pharmaceutical tablets and capsule granulates for oral administration with controlled release of the active substance.

PRIOR ART

Pharmaceutical tablets for oral use with controlled release of the active substance are known.

Controlled-rate release allows accuracy and selectivity in the action of the active substance, a reduction in its administration and, in particular, optimum utilisation of the active substance with practical and economical advantages.

For example, in treating chronic illnesses with active substances having a short emission time, the treatment requires very frequent administration (4–5 times a day) which may be poorly supported by the patient and negatively influence the results. For this reason the "delay" pharmaceutical forms, for which a single administration per day is sometimes sufficient, have been developed.

In general, such tablets of the known art consist of a central layer comprising the active substance and an outer coating layer over the whole or part of the surface to control the active substance release.

Tablet productions according to the prior art are described for example in the Japanese Patent Application No. 65688 of Apr. 15, 1983 and in the Italian Patent Application No. 23321 A/85.

Producing such tablets of the known art is very laborious and costly, as it requires the separate preparation of the mixtures for the central layer and coating layer, and then the application of the coating layer to the central layer surface.

In addition, in general before compression it is necessary to wet-granulate both the support polymer and the active principle, and this operation not only increases production costs but can also alter the active principle.

There is therefore a requirement for the production of controlled release tablets by methods based on more simple and economical operations.

SUMMARY OF THE INVENTION

The present invention relates to pharmaceutical tablets and capsule granulates for oral administration, with controlled release of the active substance, comprising scleroglucan and active substance, and pharmaceutical acceptable excipients, said tablets being prepared by mechanically mixing said substances in the solid state and directly compressing, and said granulates being prepared by mechanically disintegrating said tablets.

The physical behaviour of said tablets and said granulates in a medium at pH 2–7 is not influenced by the pH of the medium, whereas the quantity of the active substance released with time is influenced by the content of the active substance itself and of any hydrophilic and hydrophobic excipients.

DETAILED DESCRIPTION OF THE INVENTION

The pharmaceutical tablets for oral use according to the present invention are prepared by mixing together and homogenizing in the solid state the scleroglucan, the active substance and pharmaceutical acceptable excipients and directly subjecting the obtained mixture to compression. The capsule granulates, if required, are prepared from the compressed mixture by mechanical disintegration.

Possible excipients are for example polyethyleneglycol, gum arabic, aerosil, calcium chloride, sodium borate and stearic acid.

The obtained tablets and granulates do not disintegrate in aqueous solutions which simulate the physiological fluids, i.e. between pH 2 and 7, and the active substance contained in them is released over a prolonged time which varies as a function of the active substance content and, for a given active substance content, as a function of the content and type of excipients.

By adding hydrophilic excipients, such as gum arabic, it is possible to increase the release rate and also modify the release mechanism and relative profile, either by modifying the degree of swelling and gelling of the tablets and granulates when in contact with the aqueous fluid, or by partial erosion phenomena. In contrast, by adding hydrophobic excipients such as stearic acid, the release rate can be reduced by reducing the swelling and gelling.

No difference in the physical behaviour of the tablets and granulates is noted in solutions at pH 2–7.

The active substance content of the tablets and granulates is between 5 and 60% by weight, and the content of excipient substances is between 5 and 40% by weight.

To evaluate the quantity of active substance released with time an apparatus was used provided with a metal mesh drum connected to a mechanical stirrer rod to rotate the drum at a rotational speed which could be varied according to the test requirements. The drum holding the tablet or granulate is immersed in a beaker containing a buffer solution and said beaker is placed in a temperature-controlled bath. After their swelling into a gelatinous structure, the tablets and granulates remain practically unaltered for at least 7 hours when operating at a rotational speed of up to 146 r.p.m.

They release up to 70–80% of their active substance, the release being prolonged and regular with time as their structure remains unaltered and not subjected to erosion or disgregation which would result in release peaks.

The release of the active substance from the tablets and granulates according to the invention is governed by a process of diffusion through the scleroglucan matrix.

In addition to the stated characteristics, the scleroglucan matrix offers considerable protection to the active substance at the gastric level as the outer layers of the gel which forms slow down the penetration of the gastric juice into the tablet or granulate. We have, in fact, surprisingly found that the scleroglucan matrix show very interesting bioadhesion characteristics.

In particular we have found that the bioadhesion characteristics of scleroglucan are superior in comparison with the polymers usually used for the controlled release such as cellulose and cellulose derivatives and are comparable with the one of polyacrylic acid. Examples 1 to 3 given hereinafter were carried out using benzamide as active substance the solubility of which is practically uninfluenced by pH values in the 2–6.8 range, with the result that variations in the active substance release rate are independent of this parameter.

Examples 4 and 5 were carried out using theophylline as active substance.

EXAMPLE 1

A mixture of scleroglucan and benzamide in quantities of 90% and 10% respectively by weight was used to produce tablets in a single-punch press by applying a force of $4 \times 10^3$ kg. The tablets obtained had a weight of 500 mg and a diameter of 1.3 cm. One tablet was placed in a metal mesh drum connected to a mechanical stirrer rod, the drum was immersed in a beaker containing 1200 ml of an aqueous HCl solution of pH 2 and the beaker was placed in a bath temperature-controlled at 37° C.

The test was conducted by rotating the drum at 107 r.p.m. for 7 hours.

To determine the quantity of benzamide released from the tablet as a function of time, solution samples were withdrawn periodically and were analyzed by a UV spectrophotometer.

The same experiment was repeated using an aqueous solution at pH 6.8 (phosphate buffer).

The results of the two experiments are shown in the following tables.

| | Total benzamide released into solution (mg) |
|---|---|
| Experiment at pH 2 Sample withdrawal time (h) | |
| 1 | 12 |
| 2 | 18 |
| 4 | 27 |
| 7 | 36 |
| Experiment at pH 6.8 Sample withdrawal time (h) | |
| 1 | 11 |
| 2 | 18 |
| 4 | 27 |
| 7 | 35 |

The tablet appearance at the end of the experiment was identical in each case.

EXAMPLE 2

Example 1 was repeated to prepare a tablet containing 40% by weight of benzamide, which was subjected to the release test in a solution of pH 2.

The same experiment was repeated with a tablet containing 50% by weight of benzamide.

The results are shown in the following tables.

| Sample withdrawal time (h) | Total benzamide released into solution (mg) |
|---|---|
| Experiment with tablet containing 40% by weight of benzamide: | |
| 1 | 35 |
| 2 | 55 |
| 3 | 90 |
| 4 | 125 |
| Experiment with tablet containing 50% by weight of benzamide: | |
| 1 | 35 |
| 2 | 65 |
| 3 | 100 |
| 4 | 135 |

EXAMPLE 3

Example 1 was repeated to prepare a tablet containing 10% by weight of benzamide, 10% by weight of polyethyleneglycol and 80% by weight of scleroglucan, the tablet being subjected to the release test in a solution of pH 2.

The same experiment was repeated with a tablet containing 10% by weight of benzamide, 15% by weight of polyethyleneglycol and 75% by weight of scleroglucan.

The results are shown in the following tables.

| Sample withdrawal time (h) | Total benzamide released into solution (mg) |
|---|---|
| Experiment with tablet containing 10% by weight of polyethyleneglycol: | |
| 1 | 10 |
| 2 | 15 |
| 3 | 24 |
| 4 | 38 |
| Experiment with tablet containing 15% by weight of polyethyleneglycol: | |
| 1 | 10 |
| 2 | 14 |
| 3 | 24 |
| 4 | 38 |

On comparing these tables with the tables of Example 1 it will be noted that the results of the relative experiments are fairly close, however the release rate profile is different. This is demonstrated by plotting the quantity of benzamide in solution against time, to obtain a curve for Example 1 and a straight line for Example 3.

An observation of the tablets during the course of the experiments shows that the tablets containing polyethyleneglycol are subjected to higher hydration and swelling than the tablets of the preceding examples.

EXAMPLE 4

Example 1 was repeated to prepare tablets containing scleroglucan and theophylline, the theophylline content being 10%, 30% and 50% respectively by weight.

The release tests were carried out in solutions of pH 2, the results obtained being given in the following tables.

| Sample withdrawal time (h) | Total theophylline released into solution (mg) |
|---|---|
| Experiment with tablet containing 10% by weight of theophylline: | |
| 1 | 13 |
| 2 | 17 |
| 3 | 22 |
| 5 | 30 |
| Experiment with tablet containing 30% by weight of theophylline: | |
| 1 | 33 |
| 2 | 42 |
| 3 | 53 |
| 5 | 72 |
| Experiment with tablet containing 50% by weight of theophylline: | |
| 1 | 47 |
| 2 | 64 |
| 3 | 80 |
| 5 | 107 |

EXAMPLE 5

Example 1 was repeated to prepare tablets containing scleroglucan and theophylline, with a theophylline content of 50% by weight.

Said tablets were then mechanically disgregated to obtain a granulate of particle size between 0.1 and 1 mm, which was then enclosed in gelatin capsules.

The release test was carried out at pH 2, the results obtained being given in the following table.

| Sample withdrawal time (h) | Total theophylline released into solution (mg) |
| --- | --- |
| 1 | 145 |
| 2 | 170 |
| 3 | 185 |
| 5 | 215 |

We claim:

1. Pharmaceutical formulation for oral administration with controlled release of the active substance and with improved bioadhesion characteristics, comprising scleroglucan and an active substance selected from the group consisting of benzamide and theophylline in an amount of between 5 and 60% by weight and pharmaceutical acceptable excipients selected from the group consisting of polyethylene glycol, gum arabic, calcium chloride, aerosil, sodium borate and stearic acid and being present in an amount of between 5 and 40% by weight, said formulation being prepared by mechanically mixing said scleroglucan, said active substance and said pharmaceutical acceptable excipients in solid state and directly compressing to form a controlled release formulation in tablet form.

2. Pharmaceutical formulation for oral administration as claimed in claim 1 wherein the tablets are mechanically disintegrated to form a capsule granulate with a particle size of between 0.1 and 1 mm.